(12) United States Patent
Cheong et al.

(10) Patent No.: US 8,246,828 B2
(45) Date of Patent: Aug. 21, 2012

(54) METHODS FOR SELECTIVELY PRODUCING HYDROGEN AND METHANE FROM BIOMASS FEEDSTOCKS USING AN ANAEROBIC BIOLOGICAL SYSTEM

(75) Inventors: Dae-Yeol Cheong, Lakewood, CO (US); Thomas R. Clark, Lakewood, CO (US)

(73) Assignee: GeoSynFuels, LLC, Golden, CO (US)

( * ) Notice: Subject to any disclaimer, the term of this patent is extended or adjusted under 35 U.S.C. 154(b) by 473 days.

(21) Appl. No.: 12/535,503

(22) Filed: Aug. 4, 2009

(65) Prior Publication Data

US 2011/0033908 A1    Feb. 10, 2011

(51) Int. Cl.
*C02F 3/30* (2006.01)
*C02F 3/00* (2006.01)
(52) U.S. Cl. ...................................... 210/603; 210/630
(58) Field of Classification Search .................. 210/630, 210/603
See application file for complete search history.

(56) References Cited

U.S. PATENT DOCUMENTS

| | | | |
|---|---|---|---|
| 4,329,428 A | 5/1982 | Ghosh et al. | |
| 4,354,936 A | 10/1982 | Ishida et al. | |
| 5,125,977 A | 6/1992 | Grohmann et al. | |
| H1149 H | 3/1993 | Wyman et al. | |
| 5,196,069 A | 3/1993 | Cullingford et al. | |
| 5,529,692 A | 6/1996 | Kubler | |
| 5,693,296 A | 12/1997 | Holtzapple et al. | |
| 5,750,005 A | 5/1998 | Akhtar | |
| 5,865,898 A | 2/1999 | Holtzapple et al. | |
| 6,464,875 B1 | 10/2002 | Woodruff | |
| 7,540,961 B2 | 6/2009 | Hansen et al. | |
| 2004/0262220 A1 | 12/2004 | Binnig et al. | |

FOREIGN PATENT DOCUMENTS

WO    WO-92/20628 A1    11/1992

OTHER PUBLICATIONS

Cheong et al., (2006) Bacterial stress enrichment enhances anerobic hydrogen production in cattle manure sludge, *Applied Microbio. and Biotech.*, 72:635-643.

Cheong et al., (2007) "Feasibility of hydrogen production in thermophilic mixed fermentation by natural anerobes," *Bioresource Tech.*, 98:2229-2239.

Cheong et al., (2007) "Production of bio-hydrogen by mesophilic anerobic fermentation in an acid-phase sequencing batch reactor," *Biotech. and Bioeng.*, 96:421-432.

Datar et al., (2007) "Hydrogen production from fermentation of corn stover biomass pretreated with a steam-explosion process," *Int'l J. of Hydrogen Energy*, 32:932-939.

Hallenbeck et al., (2009) "Advances in fermentative biohydrogen production: the way forward?" *Trends in Biotech.*, 27:287-297.

International Search Report and Written Opinion for PCT/US2010/044203 dated Jan. 12, 2011, 7 pages.

Lay et al.(1997) "Influences of pH and moisture content on the methane production in high-solids sludge digestion," *Water Research*, 31:1518-1524.

Mosier et al., (2005) "Features of promising technologies for pretreatment of lingocellulosic biomass," *Bioresource Tech.*, 96:673-686.

Ting et al., (2007) "Production of hydrogen and methane from wastewater sludge using anerobic fermentation," *Int'l J. of Hydrogen Energy*, 32:677-682.

Uneo et al., (2007) "Production of hydrogen and methane from organic solid wastes by phase-separation of anerobic process," *Biosource Technology*, 98:1861-1865.

Westermann et al., (2007) "Maximizing renewable hydrogen production from biomass in a bio/catalytic refinery," *Int'l J. of Hydrogen Energy*, 32:4135-4141.

*Primary Examiner* — Maryam Monshipouri
(74) *Attorney, Agent, or Firm* — Goodwin Procter LLP

(57) ABSTRACT

The present invention provides a method for selective production of hydrogen and methane from a biomass feedstock in a reactor vessel maintained under anaerobic conditions by controlling moisture concentration in the reactor vessel. The method comprises the steps of introducing a biomass feedstock into the reactor vessel maintained under anaerobic conditions; introducing a bacterial inoculum into the reactor vessel to facilitate digestion of the biomass feedstock; setting a moisture concentration of the contents of the reactor vessel at a first moisture level; and collecting hydrogen gas from the reactor vessel. The method may further comprise maintaining the moisture concentration at a first moisture level or within a first moisture range. The method may additionally comprise increasing the moisture concentration of the contents of the reactor vessel to a second moisture concentration; and collecting methane gas from the reactor vessel. Switching between hydrogen and methane production is controlled by adjusting the moisture concentration of the contents of the reactor vessel.

11 Claims, 4 Drawing Sheets

METHODS FOR SELECTIVELY PRODUCING HYDROGEN AND METHANE FROM BIOMASS FEEDSTOCKS USING AN ANAEROBIC BIOLOGICAL SYSTEM

FIELD OF INVENTION

The field of the invention is the production of hydrogen and methane from biomass feedstock and, more particularly, methods and systems for the selective production of hydrogen and methane from biomass feedstock using an anaerobic biological system.

BACKGROUND

Conversion of biomass, including plants, animals, and their organic waste products and residue, currently satisfies approximately fourteen percent of the world's energy needs. Unused, discarded biomass residues from forestry, agriculture, and municipal sources are potential energy resources which at present are not well managed and thus pose significant environmental problems. More effective uses of these resources for bio-energy and related bio-products could help reduce fossil fuel emissions and mitigate greenhouse gas emissions implicated in climate change.

Current methods for converting biomass into energy include combustion, pyrolysis, gasification, biological conversion to ethanol, and biological conversion to gas including methane and (more recently) hydrogen. Combustion is a convenient method of extracting energy from biomass sources, but it can cause significant health problems associated with the production and release of soot and other chemicals into the air. Gasification may be more efficient and healthier than the direct combustion of biomass, but this process requires very high temperatures and specialized equipment. More recently, biomass containing cellulosic fiber has been converted into ethanol, but this process requires significant energy and expensive enzymes or gasification to produce ethanol. Non-cellulosic, starch- or sugar-derived ethanol is easier and less expensive to create, but it simultaneously creates pressures on food sources while not improving carbon emissions.

Anaerobic digestion (fermentation) is a well-known, low energy requiring system. Anaerobic digestion has traditionally been used in the wastewater treatment industry to reduce both the volume and the organic content of waste sludge. As anaerobic digestion technologies have evolved, the process has been applied to the treatment of a wide range of high-strength liquid waste, as well as various solid organic wastes, to reduce the chemical oxygen demand of waste effluent or to divert solid waste from disposal, and to produce bioenergy containing a mixture of methane and carbon dioxide. Conventional anaerobic digestion of organic matter results in a biogas consisting primarily of methane (60-75%) and carbon dioxide (25-40%).

Hydrogen is a promising alternative clean energy source. For example, hydrogen is not considered a greenhouse gas and it is more economical than methane at less than stoichiometric yields. While significant amounts of hydrogen can be produced from biomass feedstocks using anaerobic digestion under conditions that favor hydrogen production, a major problem in mixed anaerobic fermentation is that produced hydrogen is rapidly consumed by acetogenic and methanogenic bacteria, which convert hydrogen to acetate and methane. Thus, due to rapid "hydrogen consumption" and low hydrogen yield during anaerobic digestion, hydrogen gas has been considered only as a process control index or indicator of organic shock loading in the process of methane production.

Previous attempts to solve the problems associated with capturing hydrogen in mixed anaerobic fermentation have largely relied on a two reactor vessel system to separate hydrogen production from methane production. Such two-reactor vessel systems remove the hydrogen as it is being formed to prevent its consumption and conversion to methane. The costs of operating such a bioreactor system are dependent on the size and complexity of the system. The capital cost of the bioreactor itself is significant. Additionally, previous efforts have required the purification and/or pretreatment of bacterial colonies to enrich hydrogen-producing species and/or sterilization of the biomass feedstock to avoid hydrogen consumption, each of which adds significant capital costs and operating costs. For example, pretreatment of bacterial colonies to enrich for hydrogen-producing bacteria requires an external reaction step in a separate reactor vessel from the anaerobic digestion reactor, contributing to the cost of such approaches.

Thus, there is still an on-going need for improved methods for producing hydrogen and methane as alternative clean energy sources.

SUMMARY OF THE INVENTION

The present invention provides a method for selective production of hydrogen and methane gas from a biomass feedstock in a reactor vessel maintained under anaerobic conditions by controlling moisture concentration in the reactor vessel. Hydrogen gas is selectively produced at low moisture concentrations. For example, hydrogen gas can be selectively produced from a biomass feedstock maintained under anaerobic conditions following exposure of a bacterial inoculum containing a mixed anaerobic microbial community to a low moisture condition (also referred to herein as a severe dried condition) and digestion of the biomass feedstock at low moisture concentrations. Biogas production may then be "switched" from hydrogen to methane gas by increasing the moisture concentration in the same reactor vessel.

Selective production of hydrogen in a reactor vessel at low moisture concentrations under anaerobic conditions as described herein provides advantages compared to known methods for producing hydrogen. For example, selective hydrogen production at low moisture concentrations is achieved by adjusting or controlling the moisture concentration of the contents contained in the reactor vessel—this method does not require additional pretreatment steps (e.g., pretreatment with heat or a chemical agent) to enrich the bacterial inoculum for hydrogen-producing bacteria. Thus, the methods described herein are more cost-efficient then current methods for producing hydrogen (e.g., the methods described herein do not require a separate pretreatment vessel for conducting an additional pretreatment step). Further, unlike pretreatment methods which inactivate hydrogen-consuming bacteria (e.g., methanogens) by chemical or physical means, thus prohibiting a switch from hydrogen to methane production, the use of a low moisture concentration (or severe dried condition) within the reactor vessel provides a system for selective switching between hydrogen and methane gas production.

In one aspect, the invention provides a method of selective production of hydrogen and methane from a biomass feedstock in a reactor vessel maintained under anaerobic conditions. The method comprises the steps of introducing a biomass feedstock into a reactor vessel maintained under anaerobic conditions; introducing a bacterial inoculum into the reactor vessel to facilitate digestion of the biomass feedstock; setting a moisture concentration of contents of the reactor vessel at a first moisture level; and collecting hydrogen gas from the reactor vessel. The method may further comprise maintaining the moisture concentration at a first moisture level or within a first moisture range. The method may additionally comprise increasing the moisture concentration of the contents of the reactor vessel to a second moisture concentration; and collecting methane gas from the reactor vessel.

The biomass feedstock contained in the reactor vessel under anaerobic conditions is digested by anaerobic digestion. In certain embodiments, anaerobic digestion is conducted using a bacterial inoculum which may include a mixed population of anaerobic bacterial species such as a mixed anaerobic bacterial community containing hydrogenic, acidogenic, methanogenic, sulfate-reducing, and iron-reducing bacteria, e.g., a mixed bacterial community found in anaerobic sludge obtained from an anaerobic digestor. In an exemplary embodiment, the bacterial inoculum is exposed to a low moisture concentration (or a severe dried condition) to selectively inhibit specific bacterial species such as methanogenic bacteria. The bacterial inoculum is not pretreated with heat (e.g., dry heat or wet heat) or a chemical agent (e.g., acid, antibiotics and/or methanogic inhibitors) to enrich for specific bacterial species such as hydrogen-producing bacterial species.

It is contemplated herein that biomass feedstock and a bacterial inoculum can be introduced into the reactor vessel at different times or at the same time, in any order. In certain embodiments, biomass feedstock may be introduced into a reactor vessel containing a bacterial inoculum. In some embodiments, biomass feedstock and a bacterial inoculum are introduced into the reactor vessel substantially at the same time.

Examples of biomass feedstocks that may be digested under anaerobic conditions to produce hydrogen and/or methane, include, for example, carbonaceous material such as plant material, plant waste (e.g., agricultural waste or crop waste), plant residue, animal material, food waste, food processing waste, industrial waste, and organic waste products and residue thereof such as the organic fraction of municipal solid waste, construction waste, and demolition waste. Exemplary biomass feedstocks may include cellulose or hemicellulose. Biomass feedstock may be sterile or non-sterile.

Biomass feedstock may be pretreated or non-pretreated. Pretreatment of biomass feedstock may include, for example, ammonia fiber explosion (AFEX), steam explosion, comminution, fungal pretreatment, electrical pretreatment, acid pretreatment, alkaline pretreatment, sulfur dioxide pretreatment, and radiation pretreatment, or a combination or two or more methods. An exemplary biomass feedstock pretreatment includes ammonia fiber explosion (AFEX). In certain embodiments, the pretreatment methods disclosed herein are employed to make biomass feedstock amenable to ethanol production. In an exemplary embodiment, biomass feedstock for anaerobic digestion to produce hydrogen and optionally methane gas may be a residue from another process, e.g., production of cellulosic ethanol.

Selective production of hydrogen and methane gas from a biomass feedstock in a reactor vessel under anaerobic conditions may be controlled by varying the moisture concentration in the reactor vessel. At low moisture concentration (e.g., 85%, 83%, 80%, 78%, 76% or less), hydrogen gas is produced from the biomass feedstock maintained under anaerobic conditions. At high moisture concentration (e.g., 90%, 92%, 94%, 96%, 98% or higher), methane gas is produced from the biomass feedstock maintained under anaerobic conditions. In some embodiments, the moisture concentration in the reactor vessel may be set at a predetermined moisture concentration at the beginning of the reaction without subsequent monitoring or maintenance of the moisture concentration during the reaction. In other embodiments, the moisture concentration is monitored and maintained during the reactions to produce hydrogen and/or methane.

Moisture concentration of the contents of the reactor vessel may be increased from a first moisture level or from a first moisture range to a second moisture level or a second moisture range by rehydrating the biomass feedstock. Moisture concentration of the contents within the reactor vessel may be increased, for example, by addition of water, a liquid stream, a diluted leaching solution, steam or vapor.

The pH level of the contents within the reactor vessel may also be controlled. The pH level may be set to a neutral pH when the biomass feedstock is introduced into the reactor vessel for liquefaction and hydrolysis of the feedstock. During the production of hydrogen, the pH level of the contents within the reactor vessel may drop to about pH 4.5 to about pH 6.0. After the collection of hydrogen, the pH level of the contents within the reactor vessel may be increased to about pH 6.5 to about pH 8.0. It is understood that optimal pH levels to produce hydrogen or methane under anaerobic conditions may differ depending on the source of the biomass feedstock. In some embodiments, the pH level of the contents of the reactor vessel may be set at a predetermined pH at the beginning of the reaction without subsequent monitoring or maintenance during the reaction. In other embodiments, the pH is monitored and maintained during the reaction producing hydrogen and/or methane.

Hydrogen and methane gas may be collected using techniques well known in the art. For example, hydrogen and methane may be collected using external plastic bags such as Tedlar gas bags at low pressure. In certain embodiments, a separate gas bag can be attached to the reactor vessel to maintain constant pressure, or spring-loaded check valves for pressure relief can be included. In other embodiments, biogas may be collected in the headspace of the anaerobic digester under a floating or fixed biogas collection cover. For example, collection covers may be used as reservoirs for biogas storage at constant/low pressures. Further, volumetric gas meters or wet tip gas meters may be used to measure the gas production.

The present invention also provides a system for performing the method for selective production of hydrogen and methane from a biomass feedstock maintained under anaerobic conditions. The system comprises a reactor vessel maintained under anaerobic conditions configured to receive biomass feedstock and a bacterial inoculum; a moisture monitor/controller configured to monitor and/or control a moisture level of contents of the reactor vessel; a gas collector configured to collect hydrogen and/or methane produced in the reactor vessel from digestion of the biomass feedstock; optionally, a pH monitor/controller configured to monitor and/or control pH of the contents of the reactor vessel; and optionally, a biomass pretreater configured to pretreat the biomass feedstock prior to introduction into the reactor vessel.

These and other aspects and advantages of the invention will become apparent upon consideration of the following figures, detailed description, and claims. As used herein, "including" means without limitation, and examples cited are non-limiting.

DESCRIPTION OF THE DRAWINGS

The invention can be more completely understood with reference to the following drawings.

DETAILED DESCRIPTION

Figure 1:
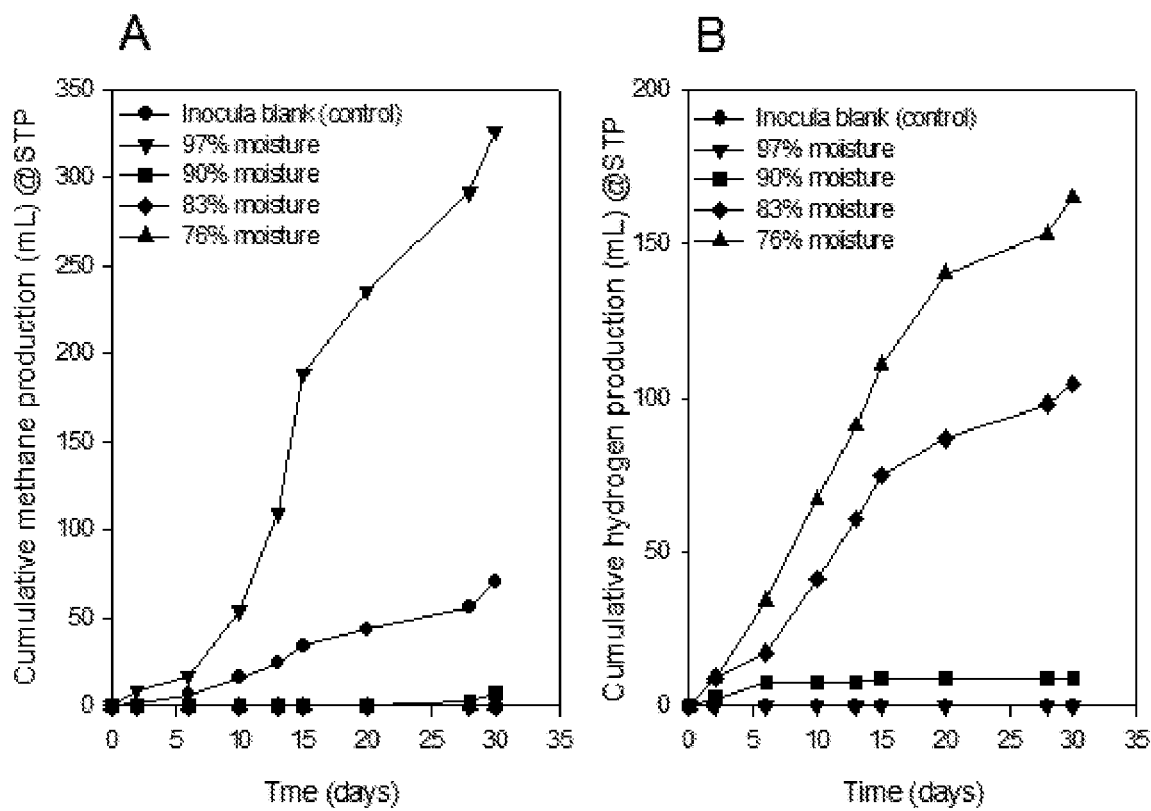
FIG. 1 is a pair of graphs showing the impact of different moisture concentrations on the cumulative methane (A) and hydrogen production (B) on AFEX (ammonia fiber expansion) pretreated corn stover.

The present invention provides a method for selective production of hydrogen and methane from a biomass feedstock in a reactor vessel maintained under anaerobic conditions. The method comprises the steps of introducing a biomass feedstock into a reactor vessel maintained under anaerobic conditions; introducing a bacterial inoculum into the reactor vessel to facilitate digestion of the biomass feedstock; setting a moisture concentration of contents of the reactor vessel at a first moisture level; and collecting hydrogen gas from the reactor vessel. The method may further comprise maintaining the moisture concentration at a first moisture level or within a first moisture range. In some embodiments, the method may additionally comprise increasing the moisture concentration of the contents of the reactor vessel to a second moisture concentration; and collecting methane gas from the reactor vessel.

Anaerobic Conditions

As used herein, the term "under anaerobic conditions" refers to reaction conditions for one or more reactions conducted in the absence or near absence (e.g., trace amounts) of oxygen, e.g., wherein a biomass feedstock is introduced into a reactor vessel containing a bacterial inoculum (also referred to herein as "anaerobic sludge" or "seed sludge") and digested by "anaerobic digestion." Bacterial inoculum may include an anaerobic microbial consortium or mixed anaerobic bacterial community including, for example, acidogenic, hydrogenic, methanogenic, sulfate-reducing, and iron-reducing bacteria as well as other bacterial species that are co-growing in a syntrophic and symbiotic relationship. Bacterial inoculum or anaerobic sludge may be obtained from anaerobic digestor (e.g., a bottom portion of an anaerobic digestor). Exemplary sources of anaerobic sludge may be obtained from, for example, anaerobic digestors operated at wastewater treatment facilities, industrial or agricultural sites, municipal waste treatment facilities, and anaerobic lagoons. In some embodiments, anaerobic sludge from several anaerobic digestor sites (e.g., at least two, three or more anaerobic digestor sites) may be combined to generate a mixed anaerobic bacterial community.

As used herein, the term "anaerobic digestion" refers to a series of processes in which microorganisms break down a biomass feedstock in the absence of or near absence of oxygen to form hydrogen and methane, among other products. Anaerobic digestion proceeds by a four-stage process. First, biomass may be hydrolyzed to be available for acidogenesis and methanogensis. Acidogenic bacteria then convert the simple sugars and amino acids into hydrogen, organic acids, ammonia, and carbon dioxide (hydrogen-producing step). Acetogenic bacteria then convert the organic acids into acetic acid and produce more hydrogen, ammonia, and carbon dioxide. Finally, the methanogenic bacteria then convert the products of the previous reactions to methane (methane-producing step).

Bacterial inoculum comprising a mixed anaerobic bacterial community may be exposed to a low moisture concentration or a "severe dried condition." As used herein, a "severe dried condition" refers to a low-moisture-stressed microenvironment. In some embodiments, a severe dried condition may be produced by setting the moisture concentration of the contents in a reactor vessel at a low moisture concentration (e.g., 85% moisture or less). In other embodiments, a severe dried condition may be obtained by covering or entrapping anaerobic sludge comprising mixed anaerobic bacterial community with a biomass feedstock in a reactor vessel. Exposure to a low moisture concentration and/or the covering and entrapment of the bacterial community contained in the anaerobic sludge by the biomass feedstock provides a low-moisture stressed environment that selectively inhibits (e.g., deactivates, reduces, or injures) the methanogenic bacterial species contained within the mixed anaerobic bacterial community. In some embodiments, the ratio of anaerobic sludge to biomass feedstock introduced into the reaction vessel to create a severe-dried condition may be a ratio of 1:5, 1:10, or 1:20 or greater. In certain embodiments, a severe dried condition may include covering anaerobic sludge with biomass feedstock in a reactor vessel and setting the moisture concentration of the contents in the reactor vessel at a low moisture concentration (e.g., 85% moisture or less). In some embodiments, biomass feedstock and the bacterial inoculum are in a slurry in the reactor vessel and the moisture concentration of the content of the reactor vessel is set at a low moisture concentration (e.g., 85% moisture or less).

Hydrogen is selectively produced following exposure of a bacterial inoculum to a severe dried condition, which may also be referred to as a dried, semi-dried, or low moisture condition. Further, selective production of hydrogen at low moisture concentrations does not require an additional step for pretreating the mixed anaerobic bacterial community such as pretreatment with heat (e.g., dry heat or wet heat) or chemical agents (e.g., acids, antibiotics and/or methanogen inhibitors), which are known in the art to enrich mixed anaerobic bacterial communities for hydrogen-producing bacteria while deactivating, reducing, or injuring hydrogen-consuming bacteria (e.g., methanogenic bacteria).

For hydrogen gas production, the gas content of the reactor vessel may include hydrogen and carbon dioxide. The percentage of hydrogen in the outflow gas may range from about 15% to about 80%, or from about 20% to about 55%. Most of the remaining gas (from about 85% to about 20%, or 80% to about 45%, respectively) may be comprised of carbon dioxide. It is understood that the ratio of hydrogen to carbon dioxide may vary with time (reaction time) during the culture period. For example, in a batch reactor at 76% moisture, the ratio of hydrogen to carbon dioxide may be 27% to 73% on day 15 of culture, 30% to 70% on day 20 of culture, and 24% to 76% on day 30 of culture. In an exemplary embodiment, methane gas should not be detected during hydrogen production.

In the methane producing step (e.g., methanogenesis), methanogenic bacteria such as hydrogen-utilizing bacteria and acetate utilizing bacteria consume hydrogen and acetate to produce methane. Without wishing to be bound by theory, methane gas is produced under anaerobic conditions when the mixed anaerobic bacterial community is comprised of active methanogenic bacteria.

For methane production, the methane content in the reactor vessel may range from about 60% to about 85%, from about 65% to about 80%, from about 70% to about 75% methane. In an exemplary embodiment, the methane content in the reactor vessel is about 65% to about 80%. Other gas components in the reactor vessel may include carbon dioxide (e.g., 40%, 35%, 30%, 25%, 20%, 15%, 10% or less carbon dioxide), hydrogen sulfide (in trace amounts), and water vapor as air (in trace amounts). In an exemplary embodiment, hydrogen gas is not detected in the outflow gas when selectively producing methane.

The process of anaerobic digestion may occur in a single vessel bioreactor or combination of bioreactors. In an exemplary embodiment, hydrogen and methane may be produced by anaerobic digestion of a biomass feedstock in a single reactor vessel with a single chamber. In a single reactor vessel, hydrogen and methane gases may be produced simultaneously or separately. In an alternate embodiment, hydrogen and methane may by produced by anaerobic digestion of a biomass feedstock in a single reactor vessel with two or more chambers to allow hydrogen and methane gases to be produced simultaneously or separately.

Biomass Feedstock

As used herein, the term "biomass feedstock" refers to any biological material, mixture, combination, derivative, or residual thereof that may be anaerobically digested to produce hydrogen and methane. Biomass feedstock may include, but is not limited to carbonaceous material such as plant material, plant waste (e.g., agricultural waste or crop waste), animal material, food waste, industrial waste, and organic waste products and residue thereof.

Exemplary plant biomass feedstock includes, but is not limited to, forest residue, mill residue, agricultural waste and residue thereof, urban wood waste and residue thereof, and dedicated energy crops. Forest residue may include, for example, logging residue; rough, rotten, or salvable dead wood; excess saplings; and small pole trees. Mill residue may include, for example, bark; coarse residues (e.g., chunks and slabs); and fine residues (e.g., shavings and sawdust). Agricultural waste and residue may include, for example, stalks and residue from e.g., corn (e.g. corn stover), wheat (e.g. wheat straw), soybeans, hay, cotton, grain sorghum, barley, oats, rice, and rye. Urban wood waste and residue may include, for example, yard trimmings, site clearing wastes, pallets, wood packaging, and other miscellaneous commercial and household wood wastes. Dedicated energy crops may include, for example, short rotation woody crops such as hybrid poplar and hybrid willow, herbaceous crops such as switchgrass, and woody non-stem residue. Exemplary feedstock includes, for example, corn stover.

In some embodiments, the biomass feedstock comprises cellulose or hemicellulose, mixtures, combinations, derivatives, or residuals thereof. Cellulose is present in plant cell walls and makes up about thirty-three percent of plant matter, and as much as 90 percent in cotton. Cellulose is substantially comprised of anhydrous glucose. Cellulose contains an enormous amount of potentially harvestable energy, but can be difficult to break down because of its crystalline structure. Hemicellulose is composed of many different sugar monomers, and unlike cellulose is easily hydrolyzed. Sources for cellulose and hemicellulose include, but are not limited to, the plant materials provided above (e.g., corn stover, wheat straw, soybeans, hay, cotton, grain sorghum, barley, oats, rice, rye, forest residue, mill residue, agricultural waste and residue thereof, urban wood waste and residue thereof, and dedicated energy crops.

Biomass feedstock may also include food waste, food processing waste, and animal waste and waste products (e.g., livestock manure). Lipid-rich waste such as glycerol and animal fat may also be used as a biomass feedstock. Organic waste such as the organic fraction of municipal solid waste, construction waste, and demolition waste may also be used as biomass feedstock. In certain embodiments, a carbohydrate-rich source or carbohydrate-rich mixture (e.g., combining two, three, four or more biomass feedstock sources) may be used for hydrogen production.

In another embodiment, biomass feedstock sources including, for example, pentose products (e.g., xylose, arabinose, mixture of polymers that contain xylose, arabinose, etc), hexose products (e.g., mannose, glucose, galactose, mixture of polymers that contain mannose, glucose, galactose, etc), volatile products ((e.g., volatile fatty acids (as acetic acid, butyric acid, and propionic acid, etc), sugar acids (as gluconic acid, uronic acid, glucouronic acid, etc), organic solvent (as ethanol, methanol, propanol, etc), and volatile organic compounds (as aldehyde, ketone, hydrocarbon, etc)), and inhibiting compounds (e.g., furfural and soluble lignin compounds) may be used for methane production.

Biomass feedstock may be sterile or non-sterile. In an exemplary embodiment, the biomass feedstock is non-sterile. Use of non-sterile biomass feedstock (compared to sterile biomass) provides numerous advantages including lower costs and suitability for commercial purposes.

Biomass feedstock may also be pretreated or non-pretreated. For example, cellulosic biomass may be first hydrolyzed with an anaerobic microorganism(s) to aid in the efficiency of conversion to hydrogen. Additionally, biohydrogen production itself may be used to pretreat lignocellulosic biomass with the resultant effluent being utilized as a feedstock for a value-added product, e.g., ammonia, acetate, acetone, butanol, ethanol, and lactate. In an exemplary embodiment, the biomass feedstock is pretreated.

Biomass feedstock pretreatments include, but are not limited to, ammonia fiber explosion (AFEX), steam explosion, comminution, fungal pretreatment, electrical pretreatment, acid pretreatment, alkaline pretreatment, sulfur dioxide treatment, and radiation pretreatment (see, e.g., Anaerobic Digestion of Biomass, p. 90-102, D. P. Chynoweth & Ron Isaacson, eds., 1987 and Mosier et al., Bioresource Technology 96:673-686 (2005)). In an exemplary embodiment, the biomass feedstock is pretreated using AFEX.

AFEX (ammonia fiber expansion (or explosion)) pretreatment involves the use of high-pressure liquid ammonia treatment followed by an explosive release of pressure (see, e.g., U.S. Pat. No. 5,865,898). The combined chemical effects and physical effects enhance the susceptibility of cellulosic biomass hydrolysis.

Steam explosion pretreatment involves exposing biomass fiber to a high pressure steam (typically 200-450 psig) (see, e.g., U.S. Pat. No. 5,865,898 and Datar et al., Int. J. Hydrogen Energy, 32: 932-939 (2007)). The resulting product is then explosively discharged to atmospheric pressure.

Comminution pretreatment involves the physical pulverizing of biomass material by, for example, grinding or pressing (see, e.g., U.S. Pat. No. 5,865,898).

Fungal pretreatment involves exposing biomass fiber to certain types of fungus, for example white rot fungus, which degrades the lignocellulosic material and makes it more easily digestible by the anaerobic bacteria (see, e.g., U.S. Pat. No. 5,750,005).

Electrical pretreatment involves an application of a short burst of high voltage to biomass placed between two electrodes. The electricity causes rapid electrical breakdown and local structural changes of the cell membrane, the cell wall, and therefore the plant tissue. This causes a dramatic increase in mass permeability and can rupture the plant tissue.

Acid pretreatment involves exposing biomass fiber to dilute acid to solubilize the lignocellulosic fiber to make it more easily digestible by the anaerobic bacteria (see, e.g., U.S. Pat. No. 5,125,977).

Alkaline pretreatment involves exposing biomass fiber to a basic compound, for example sodium hydroxide, to solubilize the lignocellulosic fiber to make it more easily digestible by the anaerobic bacteria (see, e.g., U.S. Pat. No. 5,693,296).

Sulfur dioxide pretreatment involves exposing biomass fiber to sulfur dioxide to solubilize the lignocellulosic fiber to make it more easily digestible by the anaerobic bacteria.

Radiation pretreatment involves exposing biomass fiber to irradiation (e.g., gamma, microwave, infrared, and ultraviolet) which depolymerizes biopolymers, decomposes carbohydrates, and reduces cellulose crystallinity which makes it more easily digestible by anaerobic bacteria (see, e.g., U.S. Pat. No. 5,196,069).

In certain embodiments, the pretreatment methods disclosed herein are employed to make biomass feedstock amenable to ethanol production. In an exemplary embodiment, biomass feedstock is pretreated as described herein, then hydrolyzed (e.g., enzymatic hydrolysis) and fermented with yeast to produce ethanol. After production of ethanol, the residue or residual biomass feedstock may be exposed to a low moisture concentration in a reactor vessel maintained under anaerobic conditions and anaerobically digested at low moisture concentrations to produce hydrogen gas. Optionally, the moisture concentration in the reactor vessel may be increased to a second moisture level to produce methane gas.

Methods for Selective Production of Hydrogen and Methane Gas

Selective production of hydrogen and methane gas from a biomass feedstock in a reactor vessel maintained under anaerobic conditions may be controlled by varying the moisture concentration of the contents contained within the reactor vessel. "Moisture concentration" refers to the overall moisture content (e.g., the amount or percentage of water) in the vessel reactor. Moisture concentration is the complement of "solid concentration" or "total solid concentration." Moisture concentration in both the initial feedstock and the reactor vessel may be measured indirectly by determining the "total solid" content (e.g., a total solid concentration of 20% means that the moisture concentration is 80%).

To measure the moisture concentration, the total solid is analyzed and calculated from solid, slurry, mixed liquor, according to the procedures described in "Standard Methods for the Examination of Water and Wastewater," 18th ed. American Public Health Association, Washington, D.C., 1992. "Solid content" or "total solid" may also be referred to as the residue remaining after a sample water, wastewater, semi-solid material is evaporated and the residue is dried at a specified temperature (e.g., 103° C. for 24 h) (see, e.g., Society of Agricultural and Biological Engineers (ASABE) Standards (S292.5 Oct. 1994, R2009)).

At low moisture concentrations, the outflow gas comprises hydrogen (e.g., 10%, 15%, 20%, 25%, 30%, 35%, 40%, 45%, 50%, 55%, 60%, 65%, 66%, 67%, 68%, 69% 70% or more hydrogen). At high moisture concentrations, the outflow gas comprises methane (e.g., 60%, 65%, 70%, 75%, 80%, 85%, 86%, 87%, 88%, 89%, 90%, or more methane).

In one embodiment, the moisture concentration of the contents of the reactor vessel may be set at the beginning of the reaction (e.g., at a predetermined moisture concentration) without subsequent monitoring or maintenance of the moisture concentration during the reaction. For example, moisture concentration may be set at a specified moisture concentration without subsequent monitoring in a batch process or a sequential batch process as described in greater detail below.

To produce hydrogen gas, biomass feedstock is introduced into a reactor vessel that is maintained under anaerobic conditions. The moisture concentration of the contents within the reactor vessel is set to a first moisture level. For example, the moisture concentration may be set to a first moisture level of about 85% or less, about 83% or less, about 80% or less, about 78% or less, or about 76% or less. In some embodiments, the moisture concentration may be set to a first moisture level of about 70%, 71%, 72%, 73%, 74%, 75%, 76%, 77%, 78%, 79%, 80%, 81%, 82%, 83%, 84%, or 85% moisture (compared to about 30%, 29%, 28%, 27%, 26%, 25%, 24%, 23%, 22%, 21%, 20%, 19%, 18%, 17%, 16%, or 15% total solid concentration, respectively). The biomass feedstock introduced into the reactor vessel under anaerobic conditions at a first moisture level is digested by anaerobic digestion to selectively produce hydrogen gas.

The method may further comprise collecting methane gas. After collecting hydrogen gas from the reactor vessel, the moisture concentration of the contents of the reactor vessel may be increased to a second moisture level. For example, the moisture concentration may be set to a second moisture level of about 90% or higher, about 92% or higher, about 94% or higher, about 96% or higher, or about 98% or higher moisture. In some embodiments, the moisture concentration may be set to a second moisture level of about 90%, 91%, 92%, 93%, 94%, 95%, 96%, 97%, 98% or 99% moisture (compared to about 10%, 9%, 8%, 7%, 6%, 5%, 4%, 3%, 2%, or 1% total solid concentration, respectively). The biomass feedstock introduced into the reactor vessel under anaerobic conditions at the second moisture level is digested by anaerobic digestion to selectively produce methane gas.

Moisture concentration of the contents of the reactor vessel may be increased from a first moisture level to a second moisture level by rehydrating the biomass feedstock. Rehydration of the biomass feedstock is contemplated to include any addition of moisture to the feedstock. In some embodiments, rehydration of the feedstock results in a liquid or slurry. Moisture may be increased within the reactor vessel by addition of (or dilution of the biomass feedstock with) water, a liquid stream (e.g., a buffer), or a diluted leaching solution. In some embodiments, the reactor vessel may comprise a holding tank for storing dilution liquids for addition to the reactor vessel for switching gas production from hydrogen to methane. In another embodiment, moisture may be increased in the reactor vessel by the addition of steam or vapor.

Moisture concentration may also be monitored and maintained within the reactor vessel, e.g., in a continuous or semi-continuous process. In certain embodiments, the moisture concentration may be monitored and maintained at a first moisture level or within a first moisture range for the production of hydrogen. For example, the moisture concentration may be maintained at a first moisture level of about 85% or less, about 83% or less, about 80% or less, about 78% or less, or about 76% or less. In some embodiments, the moisture concentration may be maintained at a first moisture level of about 70%, 71%, 72%, 73%, 74%, 75%, 76%, 77%, 78%, 79%, 80%, 81%, 82%, 83%, 84%, or 85% moisture (compared to about 30%, 29%, 28%, 27%, 26%, 25%, 24%, 23%, 22%, 21%, 20%, 19%, 18%, 17%, 16%, or 15% total solid concentration, respectively). Alternatively, the moisture concentration may be maintained a first moisture range of about 70% to about 85%, 72% to about 83%, about 74% to about 83%, or about 76% to about 83% moisture (compared to about 30% to about 15%, about 28% to about 17%, about 26% to about 17%, and about 24% to about 17% total solid concentration, respectively).

In other embodiments, the moisture concentration of the contents of the reactor vessel may be monitored and maintained at a second moisture level or within a second moisture range for the production of methane. For example, the moisture concentration may be maintained at a second moisture level of about 90% or higher, about 92% or higher, about 94% or higher, about 96% or higher, or about 98% or higher. In some embodiments, the moisture concentration may be maintained at a second moisture level of about 90%, 91%, 92%, 93%, 94%, 95%, 96%, 97%, 98% or 99% moisture (compared to about 10%, 9%, 8%, 7%, 6%, 5%, 4%, 3%, 2%, or 1% total solid concentration, respectively). Alternatively, the moisture concentration may be maintained at a second moisture range of about 90% to about 99%, about 90% to about 97%, about 90% to about 95%, about 90% to about 93%, about 92% to about 99%, about 92% to about 97%, or about 92% to about 95% (compared to about 10% to about 1%, about 10% to about 3%, about 10% to about 5%, about 10% to about 7%, about 8% to about 1%, about 8% to about 3%, and about 8% to about 5% total solid concentration, respectively).

The pH level of the contents within the reactor vessel may also be controlled. In the hydrogen production step, pH level of contents of the reactor vessel is set at a first pH level or within a first pH range. The first pH level may be a neutral pH or within a neutral pH range. The pH level may be adjusted to a neutral pH by, for example, the addition of HCl, NaOH, sodium biocarbonate, KOH, $NH_4OH$, lime, or calcium carbonate. In an exemplary embodiment, the biomass feedstock is introduced into the reactor vessel and the pH level is set at neutral pH for liquefaction and hydrolysis of the feedstock. During the production of hydrogen (which may be referred to as the hydrogen-producing reaction), the pH level of the contents within the reactor vessel drops to about 4.5 to about 6.0. Without wishing to be bound by theory, a drop in pH in the reactor vessel indicates a positive hydrogenic reaction.

In certain embodiments, after the collection of hydrogen gas, the pH level may be set to a second pH level or within a second pH range. In some embodiments, after the collection of hydrogen, the pH level may be increased to a second pH level or within a second pH range for the production of methane gas. It is also contemplated that rehydration (or dilution) of the biomass feedstock in the reactor vessel (to selectively produce methane) may result in an increase in pH level. Without wishing to be bound by theory, an increase in pH following a hydrogen-producing acidogenesis reaction, activates non-acidogenic bacteria (e.g., methanogenic bacteria) which leads to the production of methane.

The pH of the contents within the reactor vessel may be set at an optimal range at the beginning of an anaerobic digestion reaction for the production of hydrogen and/or methane or the pH may be monitored and maintained during the anaerobic reaction producing hydrogen and/or methane.

The pH range to produce hydrogen may range from about pH 4.5 to about pH 7.5, from about pH 5.0 to about pH 7.0, from about pH 5.5 to about pH 6.5, or from about pH 5.5 to about pH 6.0. In an exemplary embodiment, the pH range to produce hydrogen gas is between about pH 4.5 to about pH 6.0 or from about pH 5.5 to about pH 6.0.

The pH range to produce methane may range from about pH 6.5 to about pH 8.0, from about pH 6.5 to about pH 7.5, from about pH 7.0 to about pH 8.0, or from about pH 7.0 to about pH 7.5 In an exemplary embodiment, the pH range to produce methane is between about pH 7.0 to about pH 7.5.

It is contemplated herein that the optimal pH to produce hydrogen or methane under anaerobic conditions may differ depending on the source of the biomass feedstock.

The pH level of the contents within the reactor vessel may be controlled by maintaining natural buffering capacity, adding buffering chemicals, or by using a pH controller (e.g., a standard electric pH monitor probe or pH meter). The pH level of the contents within the reactor vessel may be monitored continuously or periodically. Adjustments in pH may be made by automatic addition of acid or base when the pH reaches a preset threshold to avoid a drop or increase in pH. Alternatively, adjustments in pH may be made by periodic monitoring and subsequent addition of acid or base.

The pH level of the contents within the reactor vessel may be lowered to a neutral or an acidic pH, for example, by the use of a buffer and/or the addition of an acid (e.g., HCl). The pH level of the contents within the reactor vessel may be increased, for example, to a neutral or alkaline pH by the use of a buffer and/or the addition of a base (e.g., sodium hydroxide (NaOH) or sodium biocarbonate).

Reaction time, which refers to the duration of the time beginning from feedstock loading into the reactor vessel to the completion of the hydrogenic phase for hydrogen production (or the methanogenic phase for methane production), may be varied to preferentially produce hydrogen or methane. In a closed system, reaction time may be understood as the time during which the biomass feedstock and the bacterial inoculum are in contact and producing biogas. For hydrogen production, the reaction time may be from about 1 day to about 30 days, about 1 to about 20 days, or about 2 days to about 16 days. In an exemplary embodiment, the reaction time to favor hydrogen production is about 2 days to about 16 days. The reaction time may be prolonged or shortened depending on the hydrogen-producing characteristics (for example, different biomass feedstocks). In another embodiment, the reaction time to favor methane production is about 5 to about 40 days, about 10 to about 40 days, or about 20 to about 40 days.

The hydrogen and methane gas produced by the anaerobic bacteria may be collected using techniques well known in the art. For example, when a continuous reactor is used, hydrogen and methane gas may be collected using a plastic device or gas bag such as a Tedlar gas bag. In certain embodiments, a separate gas bag may be attached to the reactor vessel to maintain constant pressure or a spring-laded check valve to relieve pressure may be employed. For larger scale or commercial production (e.g., "on-site farm" production), gas collection and storage methods will differ according to the purpose or utilization for the gas. Large scale methods may include, for example, gas collection in the upper headspace of an anaerobic digester under a floating device or fixed biogas collection cover. Collection covers may functions as reservoirs for biogas storage at constant/low pressures. Further, volumetric gas meters, wet tip gas meters, or gas chromatographs may be used to measure the gas production.

In one embodiment, biogas may be collected and measured from a batch reactor sealed with a butyl rubber stopper and an aluminum crimp (that maintains headspace of the reactor) using appropriately sized wetted syringes (including injection needles) during the culture period. Biogas composition may be monitored and determined using gas chromatography which may include use of a thermal conductivity detector.

In an exemplary embodiment, anaerobic sludge containing bacteria is gathered from a source, e.g., an anaerobic digestor at a wastewater treatment facility. It is then placed in the bottom of a reactor vessel and completely covered with a biomass feedstock, e.g., corn stover, which is pretreated, e.g., by AFEX pretreatment. Covering anaerobic sludge with biomass feedstock exposes the anaerobic bacteria to a severely-dried condition, which inhibits methanogenic bacteria. An anaerobic digestion reaction starts with low moisture concentration, e.g., 76% moisture concentration, in the reactor vessel to selectively induce hydrogen gas formation. The pH of the reactor vessel is set to a neutral pH. For hydrogen gas production, the moisture level is maintained at 76% and hydrogen gas is collected in a Tedlar gas bag. After collection of hydrogen gas, the reactor vessel can be operated to capture methane under rehydrated conditions, e.g., at a second moisture concentration of 97%, by the addition of water, an additional liquid stream, or diluted leaching solution, steam, or any vapor using the same vessel that has captured hydrogen gas. Methane gas is collected using a Tedlar gas bag.

Hydrogen and methane gases produced using the methods described herein may be utilized for any number of energy-based processes. For example, hydrogen or methane may be used for the generation of electric power by combustion or fuel cell, injection into an existing natural gas pipeline, conversion to other chemical forms including, for example, methanol and ammonia. Although the methods disclosed herein may produce methane and hydrogen separately, it is contemplated that hydrogen and methane gas may be recombined and used for the above processes and other uses. Further, some end uses, including, for example, the use of biogas in mobile engines will require compressing the gas. Prior to compression, biogas may be cleaned and conditioned. If a methane pipeline is within a reasonable distance, biogas can be sold as methane if cleaned of all impurities and pressurized to a level equal of that in the commercial delivery pipelines.

Selective production of hydrogen and methane gas production may be performed in a continuous reactor, a semi-continuous reactor, or a batch reactor. A continuous reactor may be used for scaling up production and automation of the disclosed methods (e.g., automated switching between hydrogen and methane production). A batch process may be modified to a "sequential batch process" which results in the production of hydrogen and/or methane gas from the combination of several batch reactors. In certain embodiments, the reaction to produce hydrogen and methane is conducted in a continuous reactor, e.g., a continuous-flow stirred tank reactor (CSTR). In certain embodiments, the reaction to produce hydrogen and methane is conducted in a batch reactor, e.g., an anaerobic sequencing batch reactor (ASBR).

It is contemplated that methods, systems, and processes of the claimed invention encompass scale-ups, variations, and adaptations developed using information from the embodiments described herein. For example, the invention includes pilot plant and plant-scale manufacturing processes whose feasibility is demonstrated by the laboratory-scale experiments described herein. Processes described herein may be conducted in batch, semi-continuous, and/or continuous operation. Scale-up of systems from laboratory to plant scale (e.g., for commercial production) may be performed by those of ordinary skill in the field of biogas production. For example, those of ordinary skill in this field may select process equipment, design experiments for obtaining kinetic data, develop and apply models for equipment and process design, develop economically optimum equipment and process design, and/or validate equipment and process designs via pilot plant and/or full scale reactor experiments.

Figure 4:
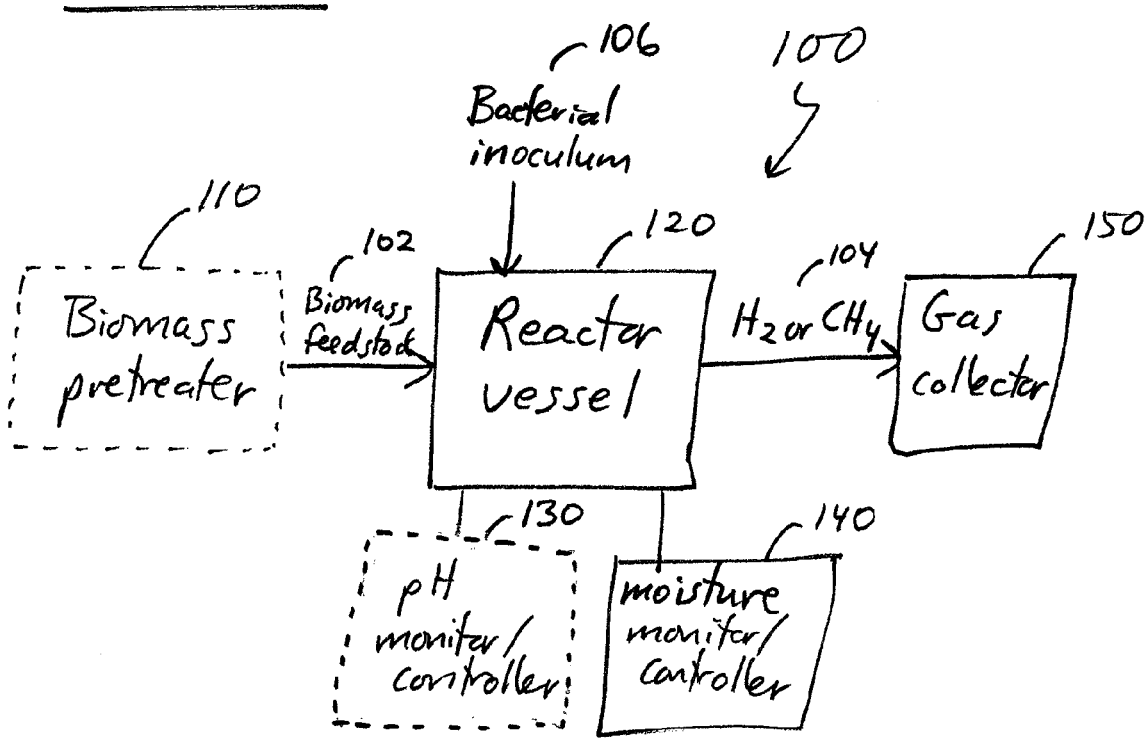
FIG. 4 is a schematic diagram of a system for the selective production of hydrogen and methane, according to an illustrative embodiment of the invention.

FIG. 4 is a schematic diagram of a system 100 for the selective production of hydrogen and methane, according to an illustrative embodiment. The reactor vessel 120 is maintained under anaerobic conditions, and receives biomass feedstock 102, which is optionally pretreated in a biomass pretreater 110, and a bacterial inoculum 106. The reactor vessel 120 is used to digest the biomass feedstock 102 under anaerobic conditions. The biomass pretreater 110 may be used for biomass feedstock pretreatments such as ammonia fiber explosion (AFEX), steam explosion, comminution, fungal pretreatment, electrical pretreatment, acid pretreatment, alkaline pretreatment, sulfur dioxide pretreatment, and radiation pretreatment. The biomass pretreater 110 is not used for the pretreatment of bacterial inoculum 106. Associated with the reactor vessel 120 is a pH monitor/controller 130 for optionally monitoring and/or controlling the pH level in the reactor vessel 120, and a moisture monitor/controller 140 for monitoring and/or controlling the moisture level in the reactor vessel 120. Hydrogen ($H_2$) or methane gas ($CH_4$) 104 produced in the reactor vessel 120 is collected by the gas collector 150. The system 100 is capable of carrying out the methods for selective production of hydrogen and methane gas described herein.

It should be understood that the order of steps or order for performing certain actions is immaterial, as long as the invention remains operable. Moreover, two or more steps or actions may be conducted simultaneously.

EXAMPLES

The following Examples are merely illustrative and are not intended to limit the scope or content of the invention in any way.

Example 1

Substrate and Inocula for Production of Hydrogen and Methane

The bacterial inocula for Examples 2-3 were obtained from the bottom portion sludge of an anaerobic digester plant at Coors Brewery (Golden, Colo.). Corn stover pretreated with ammonia fiber explosion (AFEX) (total solids: 52.3%; volatile solids: 48.5%) was used as a biomass feedstock substrate to perform the methods described in Examples 2-3. Corn stover without any pretreatment (total solids: 93.7%; volatile solids: 88.4%) was used as a control.

Example 2

A Method to Produce Hydrogen and Methane Gas

The bacterial inocula (also referred to herein as seed sludge), containing a mixed anaerobic bacterial community, was exposed to a severe dried condition as described herein to deactivate, inhibit, or injure selectively the vegetative methanogenic bacterial species from the mixed bacterial community. The batch culture method was performed in a glass serum bottle with a working volume of 100 mL. Seed sludge cultures were mixed with sodium bicarbonate and the pH was adjusted to an initial pH of about 7. Seed sludge was placed at the bottom of the serum bottle and then covered with corn stover biomass with and without pretreatment. Exposure of the cultures to a "severe dried condition" (as low-moisture-stressed microenvironment) lead to higher hydrogen/methane yields.

In one example, each seed sludge was inoculated at 10.0% (v/v) into corn stover substrate. Two sets of bottles (150 mL per bottle) for different moisture concentrations (97%, 90%, 83% and 76% (only for AFEX pretreated stover)) were prepared in duplicate. Sodium bicarbonate of 0.8 g was added to the serum bottles. The culture was adjusted to its initial pH with 5 N HCl or 5 N NaOH. The headspace of the bottles was purged with nitrogen gas to eliminate remaining oxygen from the headspace, and the bottles were sealed with butyl rubber stoppers and aluminum crimps. The bottles were then placed in a static incubator with temperature controlled at 35.0° C.±0.5° C.

Example 3

Production of Hydrogen and Methane Under Variable Moisture Conditions

Figure 2:
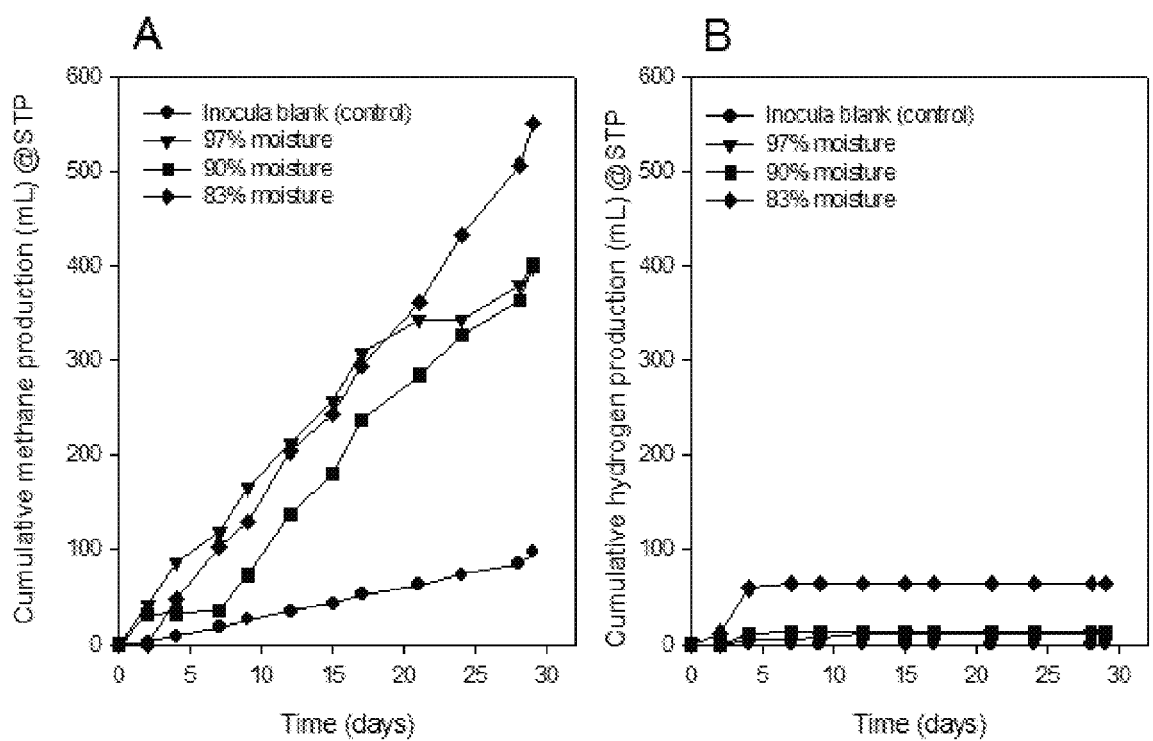
FIG. 2 is pair of graphs showing the impact of different moisture concentrations on the cumulative methane (A) and hydrogen production (B) on non-pretreated corn stover.

Hydrogen and methane production patterns varied with the moisture (solid) concentration. As shown in FIG. 1 (pretreated biomass feedstock) and FIG. 2 (non-pretreated biomass feedstock), methane production increases with increased moisture content whereas hydrogen production decreases. For example, as shown in FIG. 1A, a moisture concentration of 97% produced high methane with no hydrogen production. As shown in FIG. 1B, a moisture concentration of 76% produced a high hydrogen yield with no or little methane production. Thus, low moisture concentration (high solid concentration) enriched hydrogen-producing bacteria and deactivated hydrogen-consuming methanogens or hydrogen-consuming bacteria, increasing hydrogen production.

Non-pretreated feedstock exposed to high and low moisture concentrations did not produce significant amounts of hydrogen gas (compare FIGS. 2A and 2B). These results indicate that the use of non-pretreated biomass results in decreased hydrogen production and stimulates production of methane gas.

Figure 3:
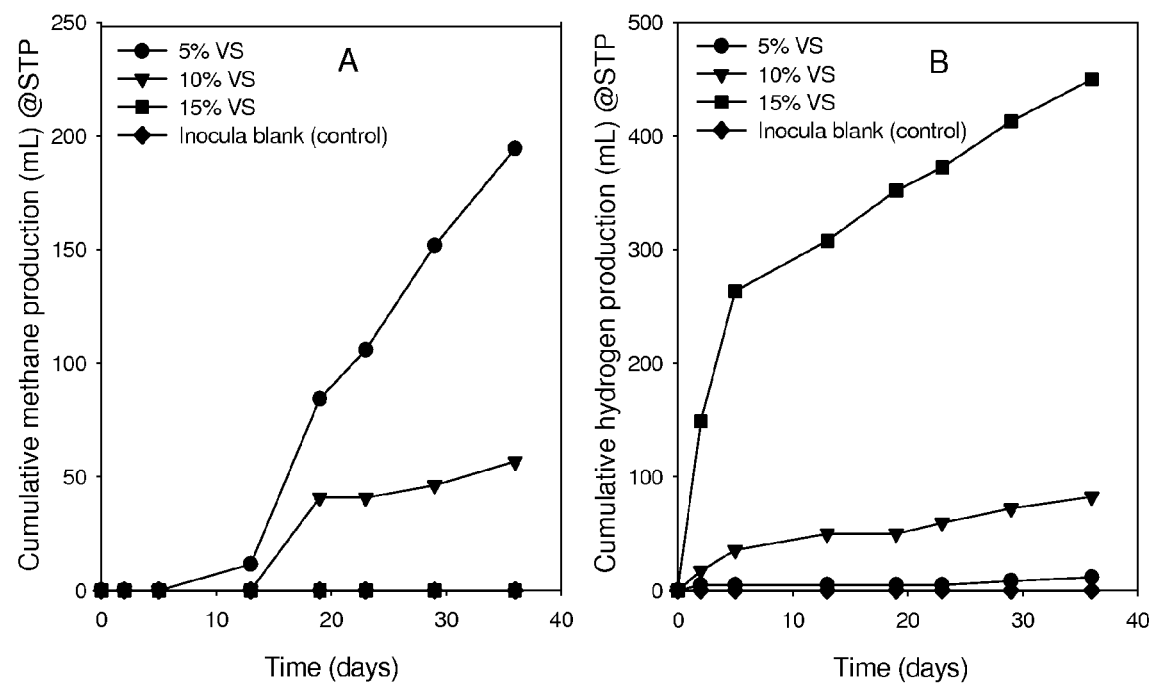
FIG. 3 is a pair of graphs showing selective methane (A) and hydrogen (B) production profiles in the anaerobic digestion fed with different solid concentrations of the residue from solid state ethanol fermentation of old corrugated cardboard (VS; volatile solid, 5%, 10%, and 15% VS, which corresponds to moisture concentrations of 95.3%, 89.5%, and 84.3%, respectively).

Further, as shown in FIG. 3, low solid concentration (5% volatile solid (VS)) of residues from solid state ethanol fermentation of old corrugated cardboard produced high methane with no hydrogen production. High solid concentration (15% VS) produced high hydrogen with no methane production. Thus, high solid concentration (low moisture concentration) can be used to selectively produce hydrogen gas compared to methane gas.

The production profiles of volatile fatty acids (VFAs) and ethanol were also determined during the anaerobic fermentation of AFEX pretreated corn stover are shown in Table 1 below. Conditions that presented higher concentrations of VFAs (at moisture concentrations of 83%) were strongly correlated with the higher hydrogen yield. The analysis of the VFAs and solvent was not conducted at moisture concentration of 76% due to the lack of free solution.

TABLE 1

| Moisture (%) | Major VFA components[h] (mg/L) | | | | | | Ethanol[g] (mg/L) |
|---|---|---|---|---|---|---|---|
| | HAc[a] | HPr[b] | i-HBu[c] | n-HBu[d] | n-HVa[e] | HCa[f] | |
| 97% | ND | ND | ND | ND | ND | ND | ND |
| 90% | 26.5 | ND | ND | 1236.5 | ND | 625 | ND |
| 83% | 3295.0 | 166.5 | 4196.5 | 2085.5 | 146.5 | 2725.0 | 100.5 |
| 76% | N/A | N/A | N/A | N/A | N/A | N/A | N/A |

[a]acetate;
[b]proprionate;
[c]iso-butyrate;
[d]n-butyrate;
[e]n-valerate;
[f]n-caproate;
[g]ethanol;
[h]volatile fatty acid components;
ND, non-detectable; and
N/A, not available to achieve liquid products from the moisture concentration.

The results in Table 1 indicate that hydrogen production is related to the butyrate-acetate-caproate fermentation type which is strongly correlates to the potential for the production of hydrogen. Acetate, propionate, butyrate, ethanol, and butanol are known as the most common anaerobic fermentation products produced by mesophilic or thermophilic Clostridium species. Non-pretreated corn stover presented non-significant amounts of VFAs and solvent (as below detection limit) in the moisture concentrations tested.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

We claim:
1. A method for selective production of hydrogen and methane from a biomass feedstock in a reactor vessel maintained under anaerobic conditions, the method comprising:
   a) introducing a pretreated biomass feedstock into a reactor vessel maintained under anaerobic conditions;
   b) introducing a bacterial inoculum into the reactor vessel to facilitate digestion of the biomass feedstock;
   c) setting a moisture concentration of contents of the reactor vessel at a first moisture level less than 85%;
   d) collecting hydrogen gas from the reactor vessel at the first moisture level;

e) increasing the moisture concentration of the contents of the reactor vessel to a second moisture level greater than 90%; and f) collecting methane gas from the reactor vessel at the second moisture level.

2. The method of claim 1, wherein step (e) comprises increasing the moisture concentration by introducing water, a liquid stream, a dilution leaching solution, steam or vapor.

3. The method of claim 1, wherein there is no chemical agent or heat pretreatment to enrich the bacterial inoculum.

4. The method of claim 1, wherein the first moisture concentration of the contents of the reactor is less than 80%.

5. The method of claim 1, further comprising maintaining a pH level of the contents of the reactor vessel at a first pH level or within a first pH range.

6. The method of claim 1, wherein the biomass feedstock is selected from the group consisting of: plant material, animal material, food water, industrial waste, and organic waste products or residual thereof.

7. The method of claim 1, wherein the biomass feedstock comprises cellulose.

8. The method of claim 1, wherein the biomass feedstock is non-sterile.

9. The method of claim 1, wherein the biomass is pretreated via a member selected from the group consisting of: acid treatment, steam explosion, and ammonia fiber-freeze explosion.

10. The method of claim 1, wherein the biomass feedstock is a residue obtained from a process to produce ethanol.

11. The method of claim 1, wherein the biomass feedstock and the bacterial inoculum are introduced into the reactor vessel substantially at the same time.

* * * * *